(12) United States Patent
Markatou et al.

(10) Patent No.: US 9,075,796 B2
(45) Date of Patent: Jul. 7, 2015

(54) TEXT MINING FOR LARGE MEDICAL TEXT DATASETS AND CORRESPONDING MEDICAL TEXT CLASSIFICATION USING INFORMATIVE FEATURE SELECTION

(71) Applicants: The National Institutes of Health, a component of the US Department of Health and Human Services, Washington, DC (US); International Business Machines Corporation, Armonk, NY (US)

(72) Inventors: Marianthi Markatou, New York, NY (US); Robert Ball, Rockville, MD (US); Taxiarchis Botsis, Rockville, MD (US); Michael D. Nguyen, Bethesda, MD (US); Emily J. Woo, Rockville, MD (US)

(73) Assignees: International Business Machines Corporation, Armonk, NY (US); The National Institutes of Health, A Component of the US Department of Health and Human Services, Washington, DC (US)

( * ) Notice: Subject to any disclaimer, the term of this patent is extended or adjusted under 35 U.S.C. 154(b) by 381 days.

(21) Appl. No.: 13/715,186

(22) Filed: Dec. 14, 2012

(65) Prior Publication Data
US 2014/0006013 A1 Jan. 2, 2014

Related U.S. Application Data

(60) Provisional application No. 61/651,210, filed on May 24, 2012.

(51) Int. Cl.
| G06F 17/28 | (2006.01) |
| G06F 17/30 | (2006.01) |
| G06F 19/00 | (2011.01) |

(52) U.S. Cl.
CPC ............ *G06F 17/28* (2013.01); *G06F 17/3061* (2013.01); *G06F 19/3443* (2013.01)

(58) Field of Classification Search
USPC ............................................................ 704/9
See application file for complete search history.

(56) References Cited

U.S. PATENT DOCUMENTS 5,693,076 A * 12/1997 Kaemmerer .................... 607/59
7,617,078 B2 * 11/2009 Rao et al. ......................... 703/2
(Continued)

OTHER PUBLICATIONS

Takemura et al.; An Extraction of Medical Knowledge on Text Mining for Ubiquitous Medicine; Enterprise Networking and Computing in Healthcare industry, 2004. Proceedings, 6th International Workshop on Publication Year: 2004, pp. 114-117.*

(Continued)

*Primary Examiner* — Abdul Azad
(74) *Attorney, Agent, or Firm* — Harrington & Smith; Louis J. Percello

(57) ABSTRACT

Techniques include performing text mining on a set of case reports in text format to determine a set of grammar rules to be used to determine whether case reports meet a medical condition. The text mining includes performing feature selection, used to determine the set of grammar rules, that combines standardized case definitions with experience of medical officers for the medical condition and outputting the set of grammar rules. Another technique includes applying grammar rule(s) to new case report(s), the grammar rule(s) previously determined at least by performing text mining comprised of performing feature selection, used to determine the set of grammar rules, that combines standardized case definitions with experience of medical officers for the medical condition. Indication(s) are output of whether the new case report(s) meet or do not meet the medical condition. The techniques may be performed by a method, an apparatus, and a program product.

20 Claims, 9 Drawing Sheets

(56) References Cited

U.S. PATENT DOCUMENTS

| | | | |
|---|---|---|---|
| 8,140,556 B2* | 3/2012 | Rao et al. | 707/759 |
| 2002/0082868 A1* | 6/2002 | Pories et al. | 705/3 |

OTHER PUBLICATIONS

Sinha A, Hripcsak G, Markatou M. Large datasets in biomedicine: a discussion of salient analytic issues. Journal of the American Medical Informatics Association 2009; 16(6):759-67.

Singleton JA, Lloyd JC, Mootrey GT, Salive ME, Chen RT. An ovevew of the Vaccine Adverse Event Repotng System (VAERS) as a surveillance system. Vaccine 1999;17(22):2908-17.

Ambert KH, Cohen AM. A System for Classifying Disease Comorbidity Status from Medical Discharge Summaries Using Automated Hotspot and Negated Concept Detection. Journal of the American Medical Informatics Association 2009;16(4):590-5.

Cohen AM. Five-way smoking status classification using text hotspot identification and error-correcting output codes. Journal of the American Medical Informatics Association 2008;15(1):32-5.

Conway M, Doan S, Kawazoe A, Collier N. Classifying disease outbreak reports using n-grams and semantic features. International Journal of Medical Informatics 2009;78(12):47-58.

Farkas R, Szarvas G, Heged s I et al. Semi-automated construction of decision rules to predict morbidities from clinical texts. Journal of the American Medical Informatics Association 2009; 16(4):601-5.

Mishra NK, Cummo DM, Arnzen JJ, Bonander J. A Rule-based Approach for Identifying Obesity and Its Comorbidities in Medical Discharge Summaries. Journal of the American Medical Informatics Association 2009;16(4):576-9.

Ong MS, Magrabi F, Coiera E. Automated categorisation of clinical incident reports using statistical text classification. Quality and Safety in Health Care Aug. 19, 2010;doi:10.1136/qshc.2009.036657.

Savova GK, Ogren PV, Duffy PH, Buntrock JD, Chute CG. Mayo Clinic NLP system for patient smoking status identification. Journal of the American Medical Informatics Association 2008;15(1):25-8.

Solt I, Tikk D, Gal V. Kardkovacs ZT. Semantic classification of diseases in discharge summaries using a context-aware rule-based classifier. Journal of the American Medical Informatics Association 2009;16(4):580-4.

DeShazo JP, Turner Am. An interactive and user-centered computer system to predict physician's disease judgments in discharge summaries. Journal of Biomedical Informatics 2010;43(2):218-23.

Yang H, Spasic I, Keane JA, Nenadic G. A Text Mining Approach to the Prediction of Disease Status from Clinical Discharge Summaries. Journal of the American Medical Informatics Association Jul. 2009;16(4):596-600.

Cohen AM, Hesh WR. A survey of current work in biomedical text mining. Briefings in Bioinformatics Mar. 2005; 6(1):57-71.

Hazlehurst B, Naleway A, Mullooly J. Detecting possible vaccine adverse events in clinical notes of the electronic medical record. Vaccine 2009;27(14):2077-83.

Melton GB, Hripcsak G. Automated detection of adverse events using natural language processing of discharge summaries. Journal of the American Medical Informatics Association 2005;12(4):448-57.

Murff HJ, Forster AJ, Peterson JF, Fiskio JM, Heiman HL, Bates DW. Electronically screening discharge summaries for adverse medical events. Journal of the American Medical Informatics Association 2003:10(4):339-50.

Wang X, Hripcsak G, Markatou M. Friedman C. Active computerized pharmacovigilance using natural language processing, statistics, and electronic health records: a feasibility study. Journal of the American Medical Informatics Association 2009;16(3):328-37.

Varricchio F. Iskander J, Destefano F et al. Understanding vaccine safety information from the vaccine adverse event reporting system. The Pediatric Infectious Disease Journal 2004:23(4):287-94.

Brown EG. Using MedDRA: implications for risk management. Drug Safety 2004:27(8):591-602.

Bousquet C, Lagier G, Lillo-Le Louet A, Le Beller C, Venot A, Jaulent MC, Appraisal of the MedDRA conceptual structure for describing and grouping adverse drug reactions. Drug Safety 2005;28(1)19-34.

Bonhoeffer J, Kohl K, Chen R et al. The Brighton Collaboration: addressing the need for standardized case definitions of adverse events following immunization (AEFI). Vaccine 2002;21(3-4);298-302.

Ruggeberg JU, Gold MS, Bayas JM et al. Anaphylaxis; Case definition and guidelines for data collection, analysis, and presentation of immunization safety data, Vaccine Aug. 1, 2007;25(31):5675-84.

Ewan PW. ABC of allergies: Anaphylaxis. British Medical Journal 1998;316(7142):1442.

Vellozzi C, Broder KR, Haber P et al. Adverse events following influenza A (H1N1) 2009 monovalent vaccines reported to the vaccine adverse events reporting system, United States, Oct. 1, 2009-Jan. 31, 2010. Vaccine 2010;28(45):7248-55.

Quality Investigation of Combo Lot No. A80CA007A of Arepanrix™ H1N1 (AS03-Adjuvanted H1N1 Pandemic Influenza Vaccine) in Canada. Canadian Ministry of Health; Mar. 12, 2010.

Reblin T. Arepanrix™ H1N1 Vaccine Authorizaton for Sale and Post-Market Activities. Canadian Ministry of Health; Nov. 12, 2009.

Uzuner O. Recognizing Obesity and Comorbidities in Sparse Data. Journal of the American Medical Informatics Association 2009;16(4):561-70.

Lewis DD, Ringuette M. A comparison of two learning algorithms for text categorization. Third Annual Symposium on Document Analysis and Information Retrieval 1994;33:81-93.

Carreras X, Marquez L. Boosting trees for anti-spam email filtering. 4th International Conference on Recent Advances in Natural Language Processing 2001.

Platt J. Sequential minimal optimization: A fast algorithm for training support vector machines. Microsoft Research; 1998. Report No. MST-TR-98-14.

Hastoe T. Tibshirani R, Friedman J. The elements of statistical learning. Second Edition ed, Springer; 2009.

Stone CJ. Hansen MH, Kooperberg C. Truong YK. Polynomial splines and their tensor products in extended linear modeling. The Annals of Statistics 1997;25(4):1371-425.

Friedman JH, Regularized discriminant analysis. Journal of the American Statistical Association 1989;84(405):165-75.

Rios G, Zha H. Exploring support vector machines and random forests for spam detection. Proceedings of the First Conference on Email and Anti-Spam (CEAS) 2004.

Han EH, Karypis G, Kumar V. Text categorization using weight adjusted k-nearest neighbor classification. Advances in Knowledge Discovery and Data Mining 2001;53-65.

Chang CC, Lin CJ. LIBSVM: a library for support vector machines. Department of Computer Science; National Taiwan University; 2001.

Yang Y, Liu X. A re-examination of text categorization methods.: ACM; 1999 p. 42-9.

Friedman M. The use of ranks to avoid the assumption of normally implicit in the analysis of variance. Journal of the American Statistical Association 1937;32(200):675-701.

Yang Y, Pedersen JO. A comparative study on feature selection in text categorization.: Citeseer; 1997 p. 412-20.

Hinrichsen VL, Kruskal B, O'Brien MA, Lieu TA, Platt R. Using electronic medical records to enhance detection and reporting of vaccine adverse events. Journal of the American Medical Informatics Association Nov. 2007;14(6):731-5.

Jha AK, Laguette J, Seger A, Bates DW. Can surveillance systems identify and avert adverse drug events? A prospective evaluation of a commercial application. Journal of the American Medical Informatics Association 2008;15(5):647-53.

Linder JA, Haas JS, Iyer A et al. Secondary use of electronic health record data: spontaneous triggered adverse drug event reporting. Pharmacoepidemiology and Drug Safety Oct. 11, 2010;19:1211-5.

Forman G. An extensive empirical study of feature selection metrics for text classification. The Journal of Machine Learning Research 2003;3:1289-305.

Sebastiani F. Machine learning in automated text categorization. ACM Computing Surveys (CSUR) 2002;34(1):1-47.

(56) References Cited

OTHER PUBLICATIONS

Belkin NJ, Croft WB. Information filtering and information retrieval: two sides of the same coin? Communications of the ACM 1992;35(12):29-38.

Androutsopoulos I, Koutsias J, Chandrinos KV, Spyropoulos CD. An experimental comparison of naive Bayesian and keyword-based anti-spam filtering with personal e-mail messages.: ACM; 2000 p. 160-7.

Bekkerman R, McCallum A, Huang G. Automatic categorization of email into folders: Benchmark experiments on Enron and SRI corpora. Center for Intelligent Information Retrieval, Technical Report IR 2004;418.

Drucker H, Wu D, Vapnik VN. Support vector machines for spam categorization. IEEE Transactions on Neural networks 1999;10(5):1048-54.

* cited by examiner

310 {
ignore: <UNIMPORTANT>

320 {
DIAGNOSIS : <ANAPHYLAXIS>
DRUG : <EPINEPHRINE>
MRESP : <major_RESPIRATORY>
<ANATOMY|throat_ANATOMY><ignore>*<swell_RESPIRATORY>
⋮
mRESP : <minor_RESPIRATORY>
<throat_ANATOMY><ignore>*<closure_RESPIRATORY>
⋮
MDERM : <major_DERMATOLOGIC>
⋮
mDERM : <minor_DERMATOLOGIC>
MCDV : <major_CARDIOVASCULAR>
GI : <minor_GASTROINTESTINAL>

330 {
exclude: <ANATOMY>
<throat_ANATOMY>
<swell_RESPIRATORY>

340 {
pattern1 : <MCDV><exclude>*<MDERM>
<MCDV><exclude>*<MRESP>
pattern2 : <MCDV><exclude>*<mDERM>
<MRESP><exclude>*<GI>
pattern3 : <mDERM><exclude*>*<mRESP><exclude*>*<GI>
⋮
pattern4 : <DIAGNOSIS>

| Classifiers | Testing Set | | | | Validation Set | | | |
|---|---|---|---|---|---|---|---|---|
| | macro-R | macro-P | macro-F* | | macro-R | macro-P | macro-F* | |
| NB | 0.794 (10) | 0.753 (4) | 0.773 | | 0.671 (11) | 0.697 (4) | 0.684 | |
| ME | 0.701 (6) | 0.863 (9) | 0.773 | | 0.577 (7.5) | 0.775 (10.5) | 0.661 | |
| DT | 0.609 (2) | 0.891 (12) | 0.724 | | 0.544 (1.5) | 0.767 (9) | 0.637 | |
| RPCT | 0.642 (4) | 0.872 (10) | 0.740 | | 0.544 (1.5) | 0.732 (6.5) | 0.624 | |
| BT | 0.881 (13) | 0.639 (2) | 0.741 | | 0.789 (12) | 0.648 (2) | 0.711 | |
| w-SVM | 0.871 (12) | 0.619 (1) | 0.724 | | 0.809 (13) | 0.619 (1) | 0.701 | |
| s-SVM | 0.642 (4) | 0.855 (7.5) | 0.734 | | 0.555 (4) | 0.795 (12) | 0.654 | |
| SB | 0.708 (8) | 0.836 (6) | 0.767 | | 0.574 (5) | 0.677 (3) | 0.622 | |
| MARS | 0.707 (7) | 0.809 (5) | 0.755 | | 0.576 (6) | 0.733 (8) | 0.645 | |
| RDA | 0.831 (11) | 0.649 (3) | 0.729 | | 0.640 (10) | 0.702 (5) | 0.669 | |
| RF | 0.642 (4) | 0.855 (7.5) | 0.734 | | 0.589 (9) | 0.817 (13) | 0.684 | |
| GAM | 0.751 (9) | 0.885 (11) | 0.813 | | 0.577 (7.5) | 0.775 (10.5) | 0.661 | |
| w-kNN | 0.576 (1) | 0.892 (13) | 0.700 | | 0.554 (3) | 0.732 (6.5) | 0.631 | |

FIG. 5: Table 1

| Classifiers | Testing Set | | | Validation Set | | |
|---|---|---|---|---|---|---|
| | macro-R | macro-P | macro-F* | macro-R | macro-P | macro-F* |
| NB | 0.789 (11) | 0.799 (4) | 0.794 | 0.584 (8) | 0.665 (3) | 0.622 |
| ME | 0.707 (7.5) | 0.809 (5.5) | 0.755 | 0.587 (10) | 0.719 (6) | 0.646 |
| DT | 0.667 (3) | 0.871 (7) | 0.756 | 0.576 (3.5) | 0.716 (5) | 0.638 |
| RPCT | 0.651 (1) | 0.877 (8) | 0.747 | 0.555 (1) | 0.795 (11) | 0.654 |
| BT | 0.869 (12) | 0.672 (2) | 0.758 | 0.894 (13) | 0.635 (2) | 0.743 |
| w-SVM | 0.883 (13) | 0.628 (1) | 0.734 | 0.882 (12) | 0.629 (1) | 0.734 |
| s-SVM | 0.710 (9) | 0.905 (11) | 0.796 | 0.577 (5.5) | 0.752 (8) | 0.653 |
| SB | 0.693 (5.5) | 0.899 (9.5) | 0.783 | 0.576 (3.5) | 0.733 (7) | 0.645 |
| MARS | 0.677 (4) | 0.944 (12) | 0.789 | 0.567 (2) | 0.816 (12) | 0.669 |
| RDA | 0.788 (10) | 0.783 (3) | 0.786 | 0.585 (9) | 0.683 (4) | 0.630 |
| RF | 0.661 (2) | 0.962 (13) | 0.783 | 0.578 (7) | 0.833 (13) | 0.683 |
| GAM | 0.707 (7.5) | 0.809 (5.5) | 0.755 | 0.589 (11) | 0.791 (10) | 0.675 |
| w-kNN | 0.693 (5.5) | 0.899 (9.5) | 0.783 | 0.577 (5.5) | 0.775 (9) | 0.661 |

FIG. 6: Table 2

| Data Set | macro-R | macro-P | macro-F | MER |
|---|---|---|---|---|
| Testing set | 0.889 | 0.691 | 0.777 | 0.058 |
| Validation set | 0.849 | 0.684 | 0.758 | 0.059 |

FIG. 7: Table 3

| Features | Classifiers | Average Metrics over both sets* | | | |
|---|---|---|---|---|---|
| | | Sens ± SE | Spec ± SE | PPV | NPV |
| Lemmas | w-SVM | 77.60% ± 5.78% | 90.35% ± 0.84% | 24.85% | 99.60% |
| | BT | 74.15% ± 5.48% | 92.75% ± 0.73% | 29.85% | 98.85% |
| Low-level patterns | w-SVM | 86.40% ± 5.07% | 90.05% ± 0.85% | 26.30% | 99.40% |
| | BT | 84.15% ± 5.01% | 92.15% ± 0.76% | 31.40% | 99.30% |
| High-level patterns | Rule-based | 79.05% ± 5.70% | 94.80% ± 0.63% | 38.40% | 99.10% |

*over testing and validation sets

FIG. 8:
Supplementary
Table 4

| Classifiers | Lemmas | | Low-level patterns | |
|---|---|---|---|---|
| | Mean-MER | SE | Mean-MER | SE |
| NB | 0.0410 | 0.0039 | 0.0380 | 0.0038 |
| ME | 0.0335 | 0.0036 | 0.0365 | 0.0037 |
| DT | 0.0355 | 0.0037 | 0.0355 | 0.0037 |
| RPCT | 0.0355 | 0.0037 | 0.0345 | 0.0036 |
| BT | 0.0800 | 0.0053 | 0.0815 | 0.0055 |
| w-SVM | 0.1015 | 0.0060 | 0.1015 | 0.0059 |
| s-SVM | 0.0350 | 0.0036 | 0.0325 | 0.0035 |
| SB | 0.0370 | 0.0038 | 0.0335 | 0.0036 |
| MARS | 0.0360 | 0.0037 | 0.0320 | 0.0035 |
| RDA | 0.0590 | 0.0045 | 0.0380 | 0.0038 |
| RF | 0.0340 | 0.0036 | 0.0315 | 0.0035 |
| GAM | 0.0315 | 0.0035 | 0.0345 | 0.0036 |
| w-kNN | 0.0370 | 0.0037 | 0.0325 | 0.0035 |

FIG. 9: Table 5

TEXT MINING FOR LARGE MEDICAL TEXT DATASETS AND CORRESPONDING MEDICAL TEXT CLASSIFICATION USING INFORMATIVE FEATURE SELECTION

CROSS-REFERENCE TO RELATED APPLICATIONS

The present application claims the benefit under 35 U.S.C. §119(e) of U.S. Provisional Patent Application No. 61/651,210, filed on May 24, 2012, the disclosure of which is hereby incorporated by reference in its entirety.

BACKGROUND

This invention relates generally to text mining and, more specifically, relates to text mining in large medical text datasets.

This section is intended to provide a background or context to the invention disclosed below. The description herein may include concepts that could be pursued, but are not necessarily ones that have been previously conceived, implemented or described. Therefore, unless otherwise explicitly indicated herein, what is described in this section is not prior art to the description in this application and is not admitted to be prior art by inclusion in this section.

The following abbreviations that may be found in the specification and/or the drawing figures are defined as follows:
AE Adverse Event
AEFI Adverse Events Following Immunizations
BOW Bag Of Words
EHR Electronic Health Record
MedDRA Medical Dictionary for Regulatory Activities
ML Machine Learning
MO Medical Officer
MR Medical Record
NLP Natural Language Processing
PT Preferred Term
SRS Spontaneous Reporting System
TC Text Classification
TM Text Mining
VAERS Vaccine Adverse Event Reporting System Biomedical research is often confronted with large datasets containing vast amounts of free text that have remained largely untapped sources of information. The analysis of these data sets poses unique challenges, particularly when the goal is knowledge discovery and real-time surveillance. See Sinha et al., "Large datasets in biomedicine: a discussion of salient analytic issues", Journal of the American Medical Informatics Association, 16(6):759-67 (2009). Spontaneous Reporting Systems (SRSs), such as the U.S. Vaccine Adverse Event Reporting System (VAERS), encounter this issue. See Singleton et al., "An overview of the Vaccine Adverse Event Reporting System (VAERS) as a surveillance system", Vaccine, 17(22):2908-17 (1999).

When extraordinary events occur, such as the H1N1 pandemic, routine methods of safety surveillance struggle to produce timely results due to the resource-intensive nature of the manual review. For instance, Medical Officers have to peruse these reporting systems and determine whether adverse effects occur, e.g., as a result of the H1N1 vaccine. Consequently, there is an urgent need to develop alternative approaches that facilitate efficient report review and identification of safety issues resulting from the administration of vaccines. Text classification (TC) provides an alternative and more efficient process by distinguishing the most relevant information from adverse event (AE) reports.

SUMMARY

Techniques are presented that include performing text mining on a set of case reports in text format to determine a set of grammar rules to be used to determine whether case reports meet a medical condition. The text mining includes performing feature selection, used to determine the set of grammar rules, that combines standardized case definitions with experience of medical officers for the medical condition. The techniques include outputting the set of grammar rules. The techniques may be performed by a method, an apparatus, and a program product.

Additional techniques are presented that include applying one or more grammar rules to one or more new case reports. The one or more grammar rules are previously determined at least by performing text mining comprised of performing feature selection, used to determine the set of grammar rules, that combines standardized case definitions with experience of medical officers for the medical condition. The additional techniques include outputting, based on the applying, one or more indications of whether the one or more new case reports meet or do not meet the medical condition. The techniques may be performed by a method, an apparatus, and a program product.

BRIEF DESCRIPTION OF THE SEVERAL VIEWS OF THE DRAWINGS

FIG. 3 is a set of grammar rules used by a rule-based classifier to classify an entry in the VAERS as anaphylaxis;

FIG. 5 is Table 1, illustrating macro-averaged metrics for ML classifiers' performance on the first feature representation (lemmas), where the ranks of classifiers are included in parentheses, and the evaluation measures and classifiers are as follows: R: Recall; P: Precision; F: F-measure; NB: Naïve Bayes; ME: Maximum Entropy; DT: Decision Trees; RPCT: Recursive Partitioning Classification Trees; BT: Boosted Trees; w-SVM: Weighted Support Vector Machines; s-SVM: SVM for Sparse Data; SB: Stochastic Boosting; MARS: Multivariate Adaptive Regression Splines; RDA: Regularized Discriminant Analysis; RF: Random Forests; GAM: Generalized Additive Model; w-kNN: Weighted k-Nearest Neighbors;

FIG. 6 is Table 2, illustrating macro-averaged metrics for ML classifiers' performance on the second feature representation (low-level patterns), where the ranks of classifiers are included in parentheses, where the evaluation measures and classifiers are as follows (it should be noted that Friedman's test indicated no statistically significant differences between the classifiers): R: Recall; P: Precision; F: F-measure; NB: Naïve Bayes; ME: Maximum Entropy; DT: Decision Trees;

RPCT: Recursive Partitioning Classification Trees; BT: Boosted Trees; w-SVM: Weighted Support Vector Machines; s-SVM: SVM for Sparse Data; SB: Stochastic Boosting; MARS: Multivariate Adaptive Regression Splines; RDA: Regularized Discriminant Analysis; RF: Random Forests; GAM: Generalized Additive Model; w-kNN: Weighted k-Nearest Neighbors;

FIG. 7 is Table 3, illustrating macro-averaged metrics for rule-based classifier's performance (high-level patterns), where misclassification error rate (MER) was also calculated, and where the evaluation measures and the classifier were as follows: R: Recall; P: Precision; F: F-measure; rule-based.

Figure 10:
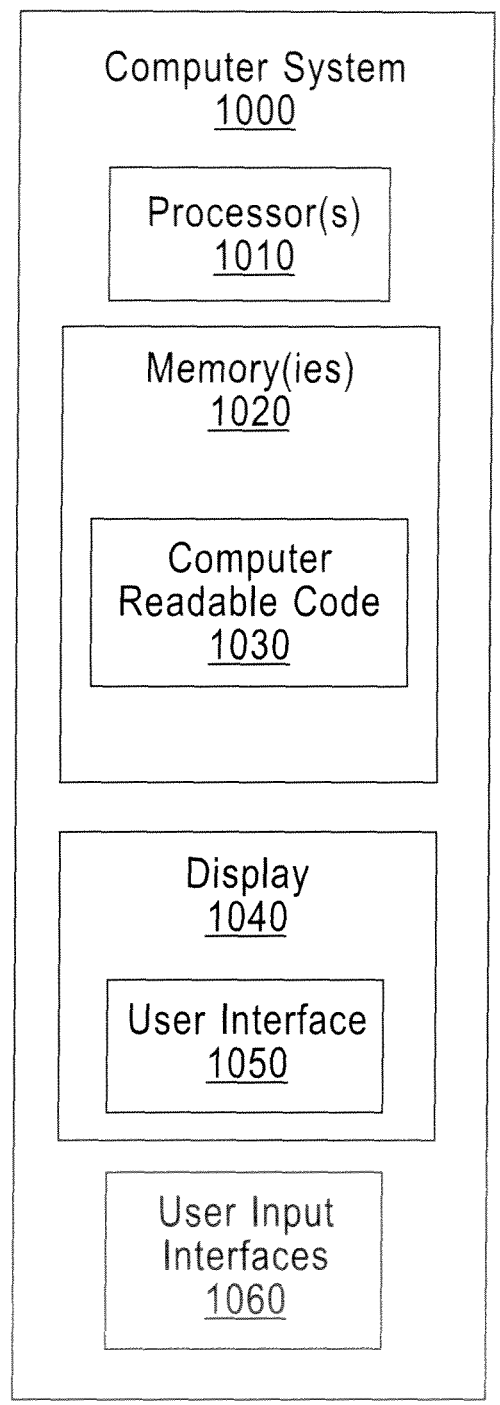

FIG. 8 is Supplementary Table 4, illustrating average sensitivity (sens), average specificity (spec) and their associated standard errors (SE) of the best performing ML classifiers and the rule-based classifier over testing and validation sets; also, the corresponding average positive predictive value (PPV), and average negative predictive value (NPV) are provided, where the classifiers are as follows: BT: Boosted Trees; w-SVM: Weighted Support Vector Machines;

FIG. 9 is Table 5, illustrating mean misclassification error rate (mean-MER) over the testing and validation data sets and the associated standard error (SE) for the different ML classifiers in the case of lemmas and low-level patterns, where the classifiers are as follows: NB: Naïve Bayes; ME: Maximum Entropy; DT: Decision Trees; RPCT: Recursive Partitioning Classification Trees; BT: Boosted Trees; w-SVM: Weighted Support Vector Machines; s-SVM: SVM for Sparse Data; SB: Stochastic Boosting; MARS: Multivariate Adaptive Regression Splines; RDA: Regularized Discriminant Analysis; RF: Random Forests; GAM: Generalized Additive Model; w-kNN: Weighted k-Nearest Neighbors; and FIG. 10 is a block diagram of a system suitable for performing exemplary embodiments of the instant invention.

DETAILED DESCRIPTION

As stated above, there is an urgent need to develop alternative approaches that facilitate efficient report review and identification of safety issues resulting from the administration of vaccines. Text classification (TC) provides an alternative and more efficient process by distinguishing the most relevant information from adverse event (AE) reports.

Medical TC is the process of assigning labels to a span of text (sentence, paragraph, or document) using trained or rule-based classifiers. For trained or rule-based classifiers, see the following: Ambert et al., "A System for Classifying Disease Comorbidity Status from Medical Discharge Summaries Using Automated Hotspot and Negated Concept Detection", Journal of the American Medical Informatics Association 2009; 16(4):590-5; Cohen A M, "Five-way smoking status classification using text hot-spot identification and error-correcting output codes", Journal of the American Medical Informatics Association 2008; 15(1):32-5; Conway et al., "Classifying disease outbreak reports using n-grams and semantic features", International Journal of Medical Informatics 2009; 78(12):47-58; Farkas et al., "Semi-automated construction of decision rules to predict morbidities from clinical texts", Journal of the American Medical Informatics Association 2009; 16(4):601-5; Mishra et al., "A Rule-based Approach for Identifying Obesity and Its Comorbidities in Medical Discharge Summaries", Journal of the American Medical Informatics Association 2009; 16(4):576-9; Ong et al., "Automated categorisation of clinical incident reports using statistical text classification", Quality and Safety in Health Care 2010 Aug. 19; doi:10.1136/qshc.2009.036657; Savova et al., "Mayo Clinic NLP system for patient smoking status identification", Journal of the American Medical Informatics Association 2008; 15(1):25-8; Solt et al., "Semantic classification of diseases in discharge summaries using a context-aware rule-based classifier", Journal of the American Medical Informatics Association 2009; 16(4):580-4. For both trained and rule-based classifiers, see the following: DeShazo et al., "An interactive and user-centered computer system to predict physician's disease judgments in discharge summaries", Journal of Biomedical Informatics 2010; 43(2):218-23; Yang et al., "A Text Mining Approach to the Prediction of Disease Status from Clinical Discharge Summaries", Journal of the American Medical Informatics Association 2009 July; 16(4): 596-600.

The utilization of Natural Language Processing (NLP) techniques may provide better classification results through improvements in text exploration. However, according to Cohen and Hersh, T C should be placed closer to the Text Mining (TM) field than the full-blown NLP field. See Cohen et al., "A survey of current work in biomedical text mining", Briefings in Bioinformatics 2005 March; 6(1):57-71. TM and NLP techniques have been used before to identify AEs in Electronic Health Records (EHR5). See the following: Hazlehurst et al., "Detecting possible vaccine adverse events in clinical notes of the electronic medical record", Vaccine, 2009; 27(14):2077-83; Melton et al., "Automated detection of adverse events using natural language processing of discharge summaries", Journal of the American Medical Informatics Association 2005; 12(4):448-57; Murff et al., "Electronically screening discharge summaries for adverse medical events", Journal of the American Medical Informatics Association 2003; 10(4):339-50; Wang et al., "Active computerized pharmacovigilance using natural language processing, statistics, and electronic health records: a feasibility study", Journal of the American Medical Informatics Association 2009; 16(3):328-37. However, the issue of a complete surveillance system that could be generalized has not been addressed yet.

Safety surveillance in VAERS (and other SRSs) has two main purposes. The first purpose is monitoring known adverse effects for unusual features or increases in reporting rate (i.e., number of reports/number of doses) while looking for potential associations with new products (e.g., H1N1 vaccine) or new demographic groups. The second purpose is looking for unexpected AEs by identifying unusual patterns. In the first case, we are more interested in the identification of the actual adverse cases, while in the second case we primarily need to know whether the identified patterns represent "real" conditions in terms of clinical syndromes.

Here, a multi-level TM approach is presented that was applied to a group of VAERS reports involving the AE of anaphylaxis for text classification purposes. This investigation of TM for anaphylaxis could serve as a model for TM in the first purpose of safety surveillance in VAERS and could also serve as the basis to generalize this work to other AEs that are acute, serious, and occur in close temporal proximity to the vaccination. Our scope was not to present a fully developed system for AE identification but rather to study patterns in the narrative of VAERS reports that are used to identify a known adverse effect. The strength of our study lies in demonstrating the feasibility of using TM on large SRS databases to exploit the information content of a new data source, other than EHRs or clinical trials data, for adverse event identification as well as in saving time and human resources.

Concerning the Vaccine Adverse Event Reporting System (VAERS), this is a passive surveillance repository that monitors the number and type of AEs that occur after the administration of vaccines licensed for use in the United States. See Varricchio et al., "Understanding vaccine safety information from the vaccine adverse event reporting system", The Pediatric Infectious Disease Journal 2004; 23(4):287-94. VAERS contains both structured (e.g., vaccination date) and unstructured data (e.g., symptom text). The VAERS case reports should be distinguished from any other type of medical documentation (e.g., discharge summaries), since it is not only experts (physicians) but also non-experts (patients and relatives) who act directly as the reporters of AEs. Therefore, special processing is needed to handle the frequent non-medical syntax and semantics.

Figure 1:
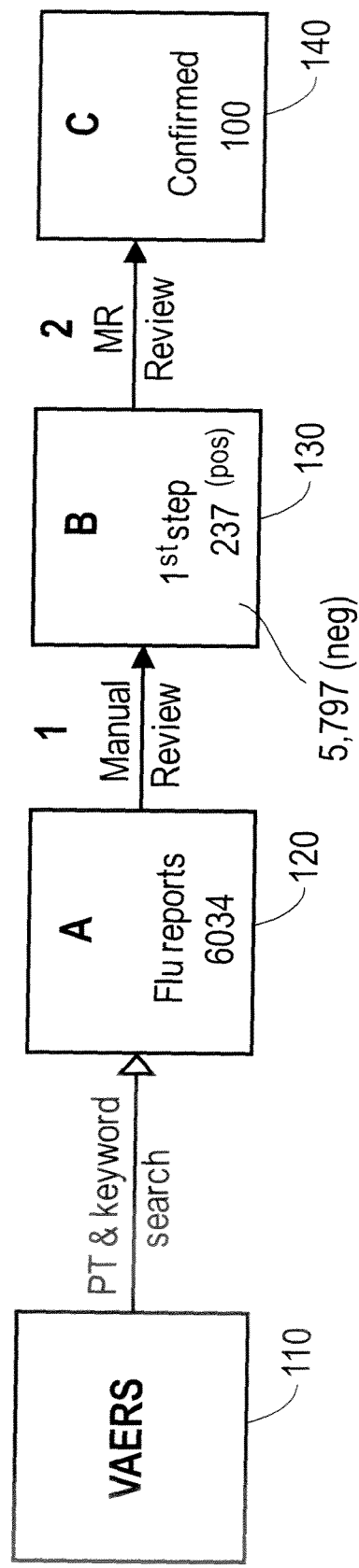
FIG. 1 is a block diagram of processing performed to determine a medical condition (e.g., anaphylaxis) based upon a medical text dataset (e.g., VAERS)

Concerning a review process for the VAER, MOs review all serious and death VAERS reports manually. Specifically, the MOs review the unstructured free text fields to identify the clinical entities in a given case report, decide upon the acquisition of additional information (e.g., request a copy of the medical records), and consider whether any regulatory action is warranted. VAERS reports are coded with Medical Dictionary for Regulatory Activities (MedDRA) Preferred Terms (PTs). See Brown E. G., "Using MedDRA: implications for risk management", Drug Safety 2004; 27(8):591-602. Non-medical data-entry personnel apply PTs to terms in AE reports according to coding conventions and algorithms; the codes are not considered to be medically confirmed diagnoses. MOs may screen and select case reports based on MedDRA codes, but the MOs cannot fully rely on the codes for the analysis of safety data, mainly due to the MedDRA limitations. The inability of MedDRA to automatically group PTs with similar meanings from different system organ classes makes PT based searches incomplete unless the searches are based on a validated Standardized MedDRA query, which are resource intensive to develop. See Bousquet et al., "Appraisal of the MedDRA conceptual structure for describing and grouping adverse drug reactions", Drug Safety 2005; 28(1):19-34. This initial process is shown in FIG. 1, where the VAERS database 110 is subjected to PT and keyword search to determine a number of flu reports 120.

The rest of the process is performed in two steps (see FIG. 1), both of which are laborious and time-consuming. Step 1 involves manual review of case reports (in this example, flu reports 120), which can number in the thousands (e.g., 6034 in this example), while Step 2 involves (e.g., manual) review of medical records (MRs) and other documentation for a smaller number of possible cases (see example for anaphylaxis; FIG. 1). The results of Step 1 are shown (classified reports 130) as 237 potentially positive (pos) reports of a particular medical condition, in this case anaphylaxis. Note that the results of Step 1 may also include the 5,797 potentially negative (neg) reports of the particular medical condition. The results of Step 2 are shown (reference 140) as 100 confirmed cases of the medical condition, in this example anaphylaxis.

Herein, a variety of TM techniques and automated classifiers are incorporated to reliably substitute the manual classification of anaphylaxis case reports at the first step (Step 1) and, thus, reduce human effort.

One technique for TM includes use of case definitions for medical conditions. There are a number of case definitions for medical conditions. The example of anaphylaxis will be used herein, but this is not a limitation on the exemplary embodiments of the instant invention.

The Brighton Collaboration develops standardized, widely disseminated, and globally accepted case definitions for a large number of Adverse Events Following Immunizations (AEFI). Each case definition is developed in a strict process that is monitored by a specific international working group of up to 20 experts and, among others, incorporates systematic literature search and the evaluation of the previous findings. See Bonhoeffer, et al., "The Brighton Collaboration: addressing the need for standardized case definitions of adverse events following immunization (AEFI)", Vaccine 2002; 21(3-4):298-302. Based on certain criteria, Brighton Collaboration defines the patterns that should be discovered in the reports of a surveillance system. Often, MOs try to match the patterns with the reported symptoms in each case report (or the medical record at Step 2 of FIG. 1). The Brighton Collaboration has developed a case definition for anaphylaxis, which is an acute hypersensitivity reaction with multi-organ-system involvement and can rapidly progress to a life-threatening reaction. See Ruggeberg et al., "Anaphylaxis: Case definition and guidelines for data collection, analysis, and presentation of immunization safety data", Vaccine 2007 Aug. 1; 25(31): 5675-84. The case definition follows:

Brighton Collaboration Case Definition of Anaphylaxis

1. Major and Minor Criteria Used in the Case Definition of Anaphylaxis

| Organ Systems | Major Criteria |
| --- | --- |
| Dermatologic or mucosal | generalized urticaria (hives) or generalized erythema angioedema (Not hereditary), localized or generalized generalized pruritus with skin rash |
| Cardiovascular | measured hypotension clinical diagnosis of uncompensated shock, indicated by the combination of at least 3 of the following: tachycardia capillary refill time >3 sec reduced central pulse volume decreased level or loss of consciousness |
| Respiratory | bilateral wheeze (bronchospasm) Stridor upper airway swelling (lip, tongue, throat, uvula, or larynx) respiratory distress - 2 or more of the following: tachypnoea increased use of accessory respiratory muscles (sternocleidomastoid, intercostals, etc.) recession cyanosis grunting |

| Organ Systems | Minor Criteria |
| --- | --- |
| Dermatologic or mucosal | generalized pruritus without skin rash generalized prickle sensation localized injection site urticaria red and itchy eyes |
| Cardiovascular | reduced peripheral circulation as indicated by the combination of at least 2 of: tachycardia and a capillary refill time of >3 sec without hypotension a decreased level of consciousness |
| Respiratory | persistent dry cough hoarse voice difficulty breathing without wheeze or stridor sensation of throat closure sneezing, rhinorrhea |
| Gastrointestinal | Diarrhoea abdominal pain Nausea Vomiting |
| Laboratory | Mast cell tryptase elevation > upper normal limit |

2. Case Definition of Anaphylaxis

| For all levels of diagnostic certainty |
| --- |
| Anaphylaxis is a clinical syndrome characterized by: sudden onset AND |
| rapid progression of signs and symptoms AND involving multiple (≥2) organ systems, as follows: Level 1 of diagnostic certainty |
| ≥1 major dermatological AND ≥1 major cardiovascular AND/OR ≥1 major respiratory criterion Level 2 of diagnostic certainty |
| ≥1 major cardiovascular AND ≥1 major respiratory criterion OR ≥1 major cardiovascular OR respiratory criterion AND ≥1 minor criterion involving ≥1 different system (other than cardiovascular or respiratory systems) OR (≥1 major dermatologic) AND (≥1 minor cardiovascular AND/OR minor respiratory criterion) Level 3 of diagnostic certainty |
| ≥1 minor cardiovascular OR respiratory criterion AND ≥1 minor criterion from each of ≥2 different systems/categories |

Common causes for anaphylaxis include allergens, drugs, and immunizations. See Ewan P W, "ABC of allergies: Anaphylaxis, British Medical Journal 1998; 316(7142):1442. According to the Brighton case definition for anaphylaxis, specific major and minor criteria are described per organ system. MOs try to discover these criteria in each case report, fit them into a pattern, and classify the report as anaphylaxis or not. For example, when the MOs read the report "immediately after vaccination the patient presented with face oedema, difficulty breathing, red eyes, wheezing and localized rash at site of injection; also complained for weakness and reported fever two days before vaccination" they classify the report as potentially positive primarily because there are at least two organ systems involved: dermatologic (face oedema, red eyes) and respiratory (difficulty breathing, wheezing). The described "rash" is localized and should not be considered as a dermatologic criterion, while "fever" and "weakness" are neither related to the vaccination nor included in the case definition. It should be mentioned that the above narrative would alarm MOs even if the sudden onset (stated by "immediately after") and the apparent rapid progression of symptoms (even though not clearly stated) were missing. Often, the time dimension is missing from VAERS reports, so MOs would still pick up this report for further review and definition of the diagnostic certainty at Step 2 in FIG. 1.

A number of methods may be used to process the VAERS database 110 (e.g., and other medical databases). For a corpus and validation set, a subset was selected of all the case reports that were submitted to VAERS following influenza A (H1N1) 2009 monovalent vaccines (see Vellozzi, et al., "Adverse events following influenza A (H1N1) 2009 monovalent vaccines reported to the vaccine adverse events reporting system United States, Oct. 1, 2009-Jan. 31, 2010", Vaccine 2010; 28(45):7248-55), covering a period from Nov. 22, 2009 to Jan. 31, 2010 (Ntotal=6,034 as shown in flu reports 120 of FIG. 1). This time-window corresponded to the same period that a thorough analysis of H1N1 reports was performed following the receipt of a safety signal from Canada in mid-November. See Varricchio et al., "Understanding vaccine safety information from the vaccine adverse event reporting system", The Pediatric Infectious Disease Journal 2004; 23(4):287-94; "Quality Investigation of Combo Lot Number A80CA007A of Arepanrix H1N1 (AS03-Adjuvanted H1N1 Pandemic Influenza Vaccine) in Canada", Canadian Ministry of Health 2010 Mar. 12; and Reblin T., "REPANRIX™ H1N1 Vaccine Authorization for Sale and Post-Market Activities", Canadian Ministry of Health, 2009 Nov. 12. Twelve MOs reviewed the reports daily (the workload share was approximately equal); their task was to use the Brighton Collaboration criteria for anaphylaxis to label them as potentially positive, requiring further investigation, or negative. Then, in one session with all MOs participating, the potentially positive reports were selected by consensus (Npos=237, as shown by the classified case reports 130 after performance of Step 1 of FIG. 1); the remaining reports 130 were classified as negative (Nneg=5,797). The classification (either positive or negative) by the MOs was the gold standard for the study.

Figure 2:
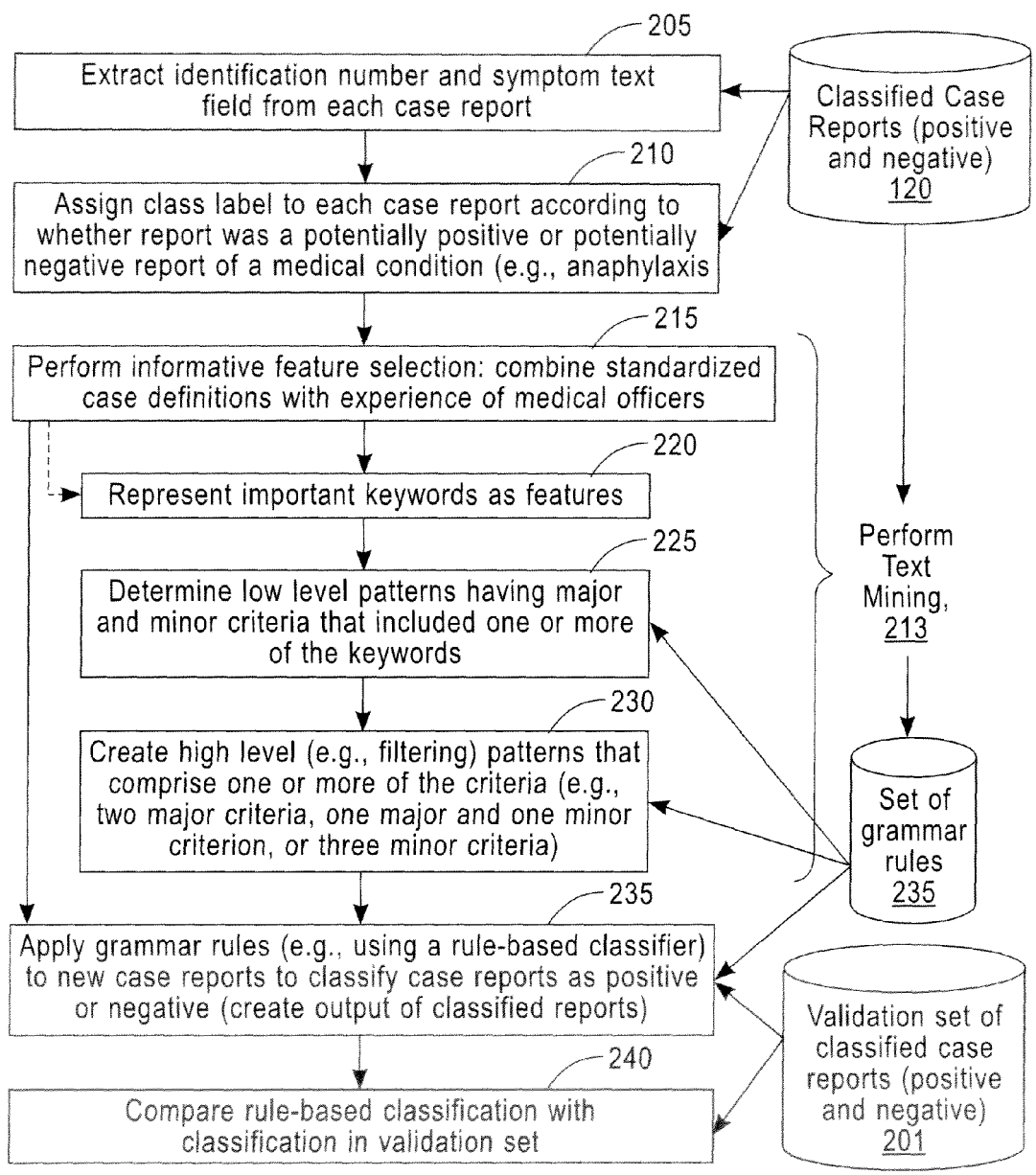
FIG. 2 is a flowchart of a method for text mining for large medical text datasets and corresponding medical text classification using informative feature selection.

FIG. 2 is a flowchart of a method for text mining for large medical text datasets and corresponding medical text classification using informative feature selection. The blocks of FIG. 2 may be method operations, operations performed by hardware (e.g., by one or more processors configured by execution of computer readable code to cause an apparatus to perform the operations, or hardware such as logic and/or an integrated circuit configured to perform the operations), or operations performed by an apparatus in response to computer readable program code configured to cause the apparatus to perform the operations. As shown in FIG. 2, the classified case reports 130 are used in certain blocks in FIG. 2.

Subsequently, an identification number and a symptom text field were extracted (see block 205 of FIG. 2), and a class label was assigned (block 210) to each case report according to the gold standard (e.g., 'pos' vs. 'neg' label for potentially positive versus negative reports, respectively). These data were included in a text file (e.g., one text file per report); all text files were further organized in a categorized corpus under two distinct categories ('pos' vs. 'neg'). The corpus in this example is classified case reports 130. Moreover, a second set (see validation set 201 of classified case reports) was created for validation purposes following a similar process: two MOs reviewed retrospectively (Feb. 1, 2010 to Apr. 28, 2010) the case reports for H1N1 vaccine and created a validation set (Nvalid=1,100) with the same distributional properties as the original set, i.e., 4% (four percent) of the case reports were potentially positive for anaphylaxis (NvalidPos=44).

Regarding feature extraction, an aspect of the study was the TM (block 213) of VAERS case reports. The starting point was the 'informative feature selection' (see block 215), that is, the combination of the Brighton Collaboration criteria with the MOs' experience. Three feature representations were used:

1. Important keywords (first feature representation=>keywords). See block 220, where important keywords are represented as features.

2. Major and minor criteria that included one or more of the above keywords. For instance, MOs considered 'epinephrine' to be equal to a major criterion. Major and minor criteria may be marked by the Brighton criteria or by the MOs. Adding the feature representing the diagnosis of anaphylaxis (sometimes stated in a case report) the feature space could be treated as a set of low-level patterns (second feature representation=>low-level patterns). See block 220, where low level patterns are determined that have major and minor criteria that included one or more of the keywords.

3. Filtering patterns that consisted of the above criteria (e.g., 'pattern1', 'pattern2', and 'pattern3'; at least two major criteria, one major and one minor criterion, and three minor criteria, respectively). Diagnosis of anaphylaxis was also considered to be a filtering pattern alone ('pattern4') and, thus, played a dual role in this work. It should be mentioned that the proportion of cases that were detected based on the explicit diagnosis of anaphylaxis were equal to 9% (16 out of 178) in the training set, 3% (2 out of 59) in the testing set and 9% (4 out of 44) in the validation set. It is noted that the symbol "%" means "percent". All filtering patterns were treated as high-level patterns (third feature representation=>high-level patterns). See block 230, where high level (e.g., filtering) patterns are created that comprise one or more of the criteria (e.g., two major criteria, one major and one minor criterion, or three minor criteria).

In further detail of the preceding description, for text mining processes and a rule-based classifier, first, the free text in the corpus was processed using the appropriate NLP methods. Second, two directions were pursued by: (i) creating the list of lemmas (hereafter called dictionary) to represent the keywords of interest (first feature representation=>keyword=>lemma) (block 220), and (ii) developing the anaphylaxis lexicon, building the grammar, tagging and parsing the free text. The grammar rules supported the extraction of major and minor criteria (second feature representation (block 225) and patterns (third feature representation (block 230) from the case reports. Using these patterns, the corresponding part of the algorithm (i.e., the rule-based classifier) classified the reports into potentially positive and negative.

The technical details of these processes are now presented in further detail. In particular, an exemplary text mining is now described.

The free text in the corpus was first normalized by converting the free text to lowercase and then by removing the punctuation marks and the stop words. The free text was also tokenized without altering the word order in the constructed list. These operations occur before block 220. From this point on, two directions were pursued, guided primarily by the predefined output, i.e., the aforementioned feature representations.

First, a list was created of 43 lemmas (called a dictionary) to represent the keywords of interest that were either identified in the Brighton case definition (see above) or suggested by the MOs as add-ons to Brighton guidelines (first feature representation=>keyword=>lemma (block 220)). Lemmas were selected to handle the disjunctions of keywords; for example 'swell' represented the disjunction: 'swelled' or 'swelling' or 'swells' or 'swollen'. Based on this principle, each case report was initially treated as a bag-of-words (BOWs). The affixes were removed from all BOWs by using the Porter Stemmer. For the Porter Stemmer, see Porter M F, "An algorithm for suffix stripping", Program 1980; 14(3): 130-7. The stemming process could not handle all disjunctions, so this process was adjusted to retain only one lemma per disjunction, e.g., 'face' for both 'face' and 'facial' since Porter Stemmer returned 'face' and 'facial', respectively.

The second direction included the anaphylaxis lexicon development, the grammar building, the tagging, and the parsing of free text. The lexicon included the lemmas (similar to those included in the dictionary) along with their semantic tags, which described the broad category into which each lemma fell; for example, 'neck', 'lip', 'tongue' 'uvula', and 'larynx' were tagged as 'ANATOMY'. However, a more specific tag was preferred for the majority of lemmas, following the format 'subcategory_CATEGORY', e.g. 'throat_ANATOMY' for 'throat' and 'major_RESPIRATORY' for 'wheez', 'bronchospasm', 'stridor', and 'distress'. This format supported the grammar structure adequately given that a lemma could fit into more than one grammar rule or even represent a major or minor criterion itself (See FIG. 3). Any out-of-lexicon items as well as numbers were tagged as 'UNIMPORTANT' by the semantic tagger. Also, the lexicon handled a few abbreviations, such as 'sob' (stands for 'shortness of breath').

The grammar rules supported the extraction of major and minor criteria from the case reports and the subsequent definition of filtering patterns (block 230). To accomplish these tasks, the grammar rules 235 were divided as follows (see also FIG. 3, which is a set of grammar rules used by a rule-based classifier to classify an entry in the VAERS as anaphylaxis) (Note that these rules are basically the patterns that were found in blocks 220/225/230):

i. One supporting rule 310 representing lemmas or numbers that were tagged as 'UNIMPORTANT'; this rule was formed by one element only.

ii. Eight basic rules 320 representing the major and minor criteria, as well as the diagnosis of anaphylaxis; these rules were formed by one or more 'important' lemmas and optional repetitions of the supporting rule.

iii. One excluding rule 330 representing the 'important' lemmas that failed to fit into any of the basic rules; this rule was formed by one element only.

iv. Four advanced rules 340 representing the filtering patterns; these rules were formed by two or three basic rules and optional repetitions of the excluding rule.

Python (version 2.6.4) was the tool used for both the TM of case reports and the development of the rule-based classifier. The block 213 therefore produces a set of grammar rules 235.

Concerning the patterns, an example is now presented with pattern1. pattern1: <MCDV><exclude>*<MDERM> contains three nested rules as follows:

1-MCDV rule: this rule returns any major cardiovascular symptom (as this is defined in the Brighton collaboration case definition);

2-MDERM rule: this rule returns any major dermatological symptom (as this is defined in the Brighton collaboration case definition);

3-exclude rule: this rule collects all the "garbage", i.e. those tokens (e.g., words) that form a criterion only as a part of a multi-token; for example, the token "throat" means nothing if it does not come with "swollen". Therefore, this rule allows the MCVD and MDERM to be combined and equate to pattern 1 (or diagnostic level 1 as per Brighton Collaboration definition).

The * (asterisk) means that there might be 0 (zero) or a number of "exclude" occurrences between the symptoms of interest. The position of the * indicates where these occurrences might be located.

All other patterns have the same interpretation as above.

The grammar rules 235 may be applied (e.g., using a rule-based classifier) to new case reports (e.g., as embodied in the validations set 201 of classified case reports, although the classification is not used) to classify case reports as positive or negative. The classified case reports are output (e.g., to a file in memory). See block 235. In block 245, the system can compare the rule-based classification with the classification in validation set.

A number of supervised machine learning (ML) classifiers that have been previously found to be the appropriate solutions for TC problems were trained. Most of these have been also used for medical TC (binary or not). The ML classifiers were as follows: Naïve Bayes (NB) (5), Maximum Entropy (ME) (27), Decision Trees (DT) (6), Recursive Partitioning Classification Trees (RPCT) (28), Boosted Trees (BT) (29), Weighted Support Vector Machines (w-SVM) (3;4), SVM for Sparse Data (s-SVM) (30), Stochastic Boosting (SB) (31), Multivariate Adaptive Regression Splines (MARS) (32), Regularized Discriminant Analysis (RDA) (33), Random Forests (RF) (34), Generalized Additive Model (GAM) (31), and Weighted k-Nearest Neighbors (w-kNN) (35). The splitting rules that were used by the decision tree classifiers (DT, RPCT and BT) should not be confused with the advanced grammar rules that represented the filtering patterns and were used by the rule-based classifier, as it was described above. For this reason, the decision tree classifiers and the rule-based classifier could not form a homogeneous group in a hypothetical comparison with the other classifiers.

An issue with ML classifiers is that these classifiers assign equal weights to all classes, no matter their rarity; this may affect their performance in favor of the commonest class. Thus, we included a weight parameter into the training process that allowed us to handle the problem of class imbalance; for instance, libSVM tool (library for SVM) allows the addition of the weight parameter to the training process (36). The weight for each class was calculated by the formula proposed by Cohen (4):

$$w_{class} = (N_{total} - N_{class})/N_{total},$$

where Ntotal is the total number of cases and Nclass the number of cases per class. Our weighted approach was also applied to BT, GAM, and s-SVM.

Python (version 2.6.4), several packages in R-statistics (version 2.11.1), and libSVM tool were used for the training of binary classifiers, as well as for the calculation of metric values in the testing and validation sets.

Concerning evaluation metrics and statistical analysis, for evaluating the performance of class-labeling by the classifiers, the macro-averaging of standard recall (R→macro-R), precision (P→macro-P), and F-measure (F→macro-F) were used. macro-R and macro-P are preferable here since they are dominated by the more rare 'pos' category (37). macro-P and macro-R were analyzed using Friedman's test that avoids the normality assumption and analyzes the ranks of classifiers within the data sets (38). Moreover, the test is appropriate for use with dependent observations, which is the case here, because classifiers were tested using the same data sets. The original level of significance of 0.05 was adjusted by Bonferroni to account for multiplicity in testing (thus, the level of the test was 0.0125, adjusted further for multiple comparisons to 0.001).

An exploratory error analysis was performed by presenting the mean misclassification error rate (mean-MER) for each classifier over the data set. Each classifier's SE is computed first on each data set (testing or validation) using the formula:

$$\left[\frac{\hat{p}_{ij}(1-\hat{p}_{ij})}{n_i}\right]^{1/2},$$

where n, i=1,2 is 1508 or 1100 respectively and $\hat{p}_{ij}$, j=1, ..., 13 is the error rate of the classifier on the testing and validation set. The mean-MER is obtained by averaging the individual data set dependent error rates and the associated SE is computed using a formula that adjusts for the different sizes of the data sets.

Furthermore, the impact of specific features on the classification was evaluated by computing the information gain for each unique lemma, low- and high-level pattern; information gain is employed as a term-goodness criterion for category prediction and is based on the presence or absence of a term in a document (39). The FSelector package in R-statistics (version 2.11.1) and the training set were used for the corresponding calculations.

Figure 4:
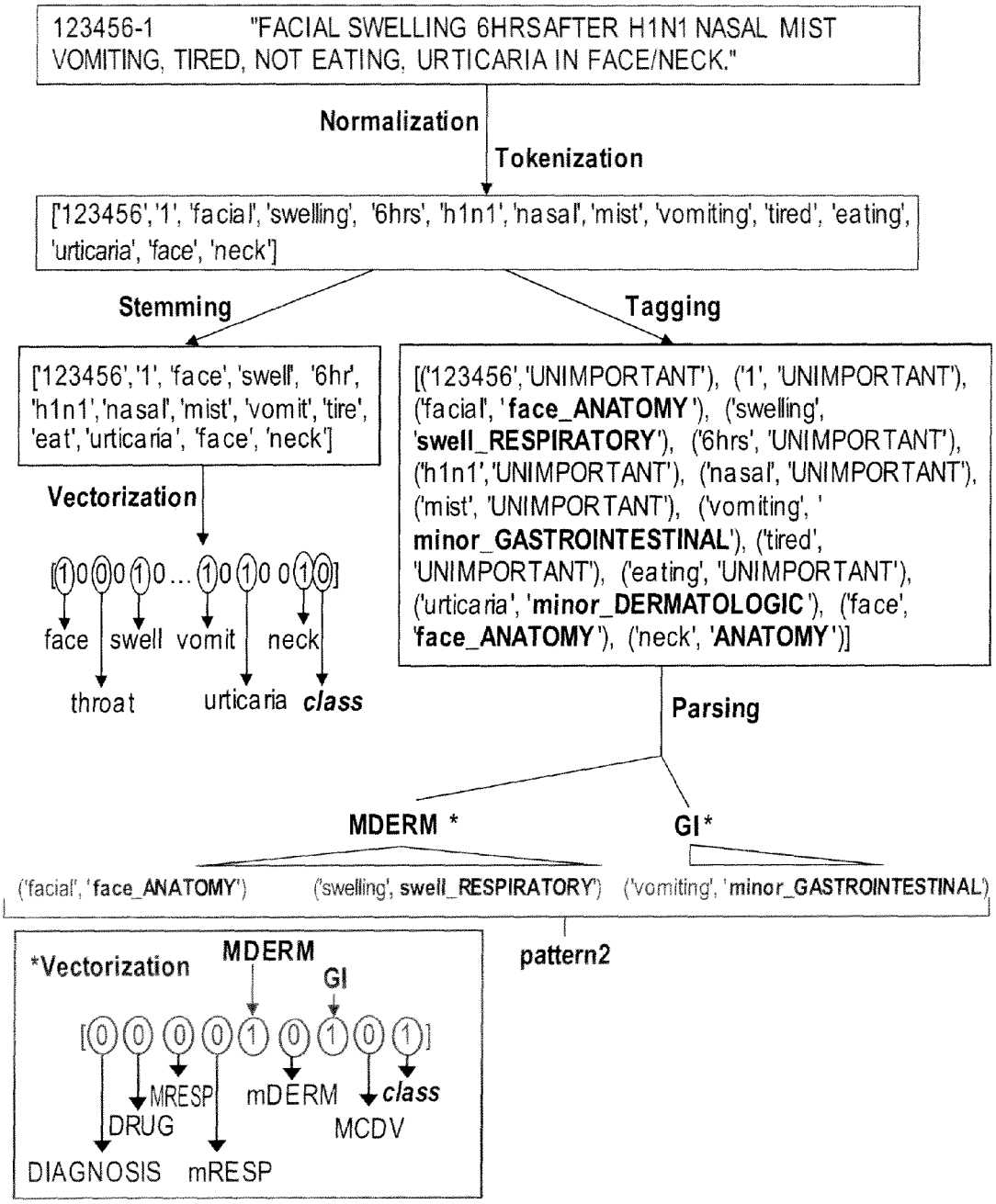
FIG. 4 presents an example of text mining results using an exemplary embodiment of the instant invention.

Results will now be described. For text mining results, the application of the instant TM techniques and the vectorization of the TM results are shown in FIG. 4. The same processes were applied to all reports (both in the corpus and the validation set). The bag-of-lemmas (BOLs) representing a case report was compared against the dictionary and a vector of binary values was constructed to indicate the presence or absence of dictionary entries in the case report; the vector (hereafter called type I vector) was extended by one position to include the class label of the report. The whole process is presented in the left branch of FIG. 4.

The semantic tagger assigned tags to the lemmas of each case report, while the parser interpreted the grammar to fit each tagged lemma into a rule; the rules were executed in order. Thus, the parsing process returned the low- and high-level patterns (FIG. 4, right branch). Again, a binary vector was created to indicate the presence or absence of the low-level patterns in each class-labeled report; each vector (hereafter called type II vector) had nine positions corresponding to the eight low-level patterns plus the class label. As for the high-level patterns no vectorization was performed since the rule-based classifier processed this output directly by classifying a case report as potentially positive when the parser output matched any of 'pattern1', 'pattern2', 'pattern3', or 'pattern4'; the report was otherwise classified as negative. The rule-based classification was straightforward and was applied to the case reports of all sets without getting into any training process.

On the other hand, in order to examine ML classifiers, all vectors (both type I and type II) of the original set were randomly split into a training and a testing set following the 75%-25% splitting rule (Ntrain=4,526 and Ntest=1,508, respectively). Both sets had the same distributional properties, i.e. 4% of the case reports were potentially positive for anaphylaxis. The performance of rule-based and ML classifiers over the testing and validation sets is presented in Tables 1-3 (shown in FIGS. 5-7). Supplementary Table 4 (FIG. 8) presents the average (over testing and validation sets) sensitivity and specificity and their associated standard errors, as well as the positive and negative predictive value of the best (across metrics) performing machine learning classifiers and rule-based classifier. Note here the equivalent performance of these classifiers in terms of all metrics presented. Yet, the rule-based classifier saved considerable computational time since it did not have to be trained, a process that was followed for w-SVM and BT, i.e. the best ML classifiers. Moreover, the w-SVM and BT classifiers were also using features extracted from the Brighton Collaboration case definition and that, to a large extent, accounts for their good performance. Further analysis was performed for macro-averages and MER (see next paragraph).

Concerning quantitative and qualitative error analysis, the null hypothesis of no difference, on average, among the ML classifiers in terms of macro-R for lemmas was rejected by Friedman's test (test statistic=12.37; p-value=0.000058, with F12,12 distribution). Bonferroni corrected multiple comparisons (a=0.0125) indicated that BT, w-SVM classifiers performed best in terms of macro-R but were statistically equivalent to NB, RDA or GAM. Notice that macro-R is equivalent to a function of sensitivity. MER analysis indicated that the mean-MER associated with BT and w-SVM classifiers was 0.08 (SE=±0.0053) and 0.1015 (SE=±0.006), respectively; this was 2.5 and 3.2 times higher than the smallest mean-MER among the equivalent classifiers (Table 5, FIG. 9). Additionally, the higher variability of these two classifiers as compared with the remaining classifiers should be noted. Therefore, higher macro-R comes at the expense of a higher mean-MER (and associated SE). Similarly, the null hypothesis of no differences, on average, among the ML classifiers in terms of macro-P was rejected by Friedman's test (test statistic=4.2346; p-value=0.0092). Bonferroni, adjusted multiple comparisons, indicated that the worst performance, in terms of macro-P, was achieved by BT and w-SVM classifiers, while GAM exhibited the best performance. GAM, RF, w-KNN, ME, DT, RPCT and s-SVM were statistically equivalent in terms of macro-P.

Similar results were obtained for low-level patterns. Specifically, BT and w-SVM classifiers performed best in terms of macro-R with NB, ME, RDA and GAM being statistically equivalent to BT and w-SVM. Our error analysis indicated higher mean-MER for the latter classifiers [for BT and w-SVM were 0.0815 (±0.0055) and 0.1015 (±0.0059), respectively]. These rates were two and three times higher the minimum mean-MER obtained from the group of equivalent to the best performing classifiers. In terms of macro-P, BT and w-SVM exhibited the worst performance, while best performers were RF and MARS. Statistically equivalent to the latter were GAM, w-KNN, DT, ME, SB, s-SVM and RPCT. The error analysis attributed a mean-MER of 0.032 (SE: ±0.0035) to RF and MARS, which is the smallest among all.

For the rule-based classifiers the mean-MER over the testing and validation set was 0.0585 (SE=±0.00465). This error rate was smaller than the best performing ML classifiers, while the performance in terms of macro-recall/precision was equivalent. Moreover, the mean macro-R was 0.8690 (SE=±0.00674), the mean macro-P was 0.6875 (SE=±0.00919), and the mean macro-F was 0.7675 (SE=±0.00839).

In addition to the aforementioned quantitative error analysis, we evaluated the classification performance of the ML classifiers using the Area Under the ROC Curve (AUC). There are several compelling reasons as to why the AUC is appropriate for quantifying the predictive ability of classifiers. One reason being the use of AUC for testing whether predictions are unrelated to true outcomes is equivalent to using the Wilcoxon test. The best performing classifiers when AUC was used were BT and w-SVM. The AUC of BT when lemmas were used in the testing and validation set was, respectively, 0.9234 (95% Confidence Interval (CI) was [0.9198, 0.9270]) and 0.7888 (95% CI was [0.7771, 0.8006]). The corresponding values of the AUC and 95% CI when low-level patterns were used for the BT classifier and for testing and validation set, respectively, were 0.8686 (95% CI was [0.8636, 0.8737]) and 0.8944 (95% CI was [0.8896, 0.8992]). For the w-SVM and for lemmas in testing and validation sets we obtained an AUC of 0.8706 and 0.8087, respectively, with corresponding 95% CI given as [0.8662, 0.8750] and [0.7989, 0.8185]. These values indicate equivalent performance of BT and w-SVM classifiers in terms of their predictive ability of identifying truly positive reports.

We also performed a qualitative error analysis aiming at understanding if any patterns are present that allow the misclassification of reports as negative when they are truly positive. The total number of false negative (FN) reports, in both testing and validation sets, returned by the three best performing classifiers (rule-based, BT and w-SVM) was 36 (16 and 20 in the testing and validation set, respectively). None of these reports contained the word "anaphylaxis" and all were missing an equivalent diagnosis. MOs examined, at a second stage, these 36 reports and reclassified as truly positive 15 of them (2 and 13 in the testing and validation set, respectively). Recall that the total number of truly positive reports in both sets equals 103. Our best performing rule-based classifier misclassified falsely as negative only 7 of these reports. The symptom text of the 15 reports and more details about their qualitative error analysis are included below in a section entitled "Qualitative Error Analysis for Symptom Text".

The feature analysis identified six lemmas ('epinephrin', 'swell', 'tight', 'throat', 'anaphylaxi', 'sob') with very similar information gain results. The diagnosis of anaphylaxis and epinephrine were among the most predictive features too, when they were treated as low-level patterns, along with major and minor respiratory and major dermatologic criteria. Regarding high-level patterns all ('pattern1', 'pattern2', and 'pattern4' that represented the diagnosis of anaphylaxis) were equivalent in terms of information gain, excluding 'pattern3'. The latter should be attributed to the extremely low (1.12%) or zero frequency of 'pattern3' in the potentially positive and negative reports of the training set, respectively. In all the other cases the frequency of the most important predictive features was remarkably higher in the subset of the potentially positive reports.

A discussion of the study now follows. In this study, we examined the effectiveness of combining certain TM techniques with domain expert knowledge in the case of VAERS for TC purposes; to our knowledge, no previous efforts have been reported for TM and medical TC in VAERS or any other SRS, despite the fact that various methods have been applied before to other data sources showing the potential for AE identification. For example, NLP methods have been applied to discharge hospital summaries (17) and other data mining methods to structured EHR data (40-42). Our validated results showed that TM in any level could effectively support TC in VAERS. For example rule-based, BT and w-SVM classifiers appeared to perform well in terms of macro-R, still with some MER cost. A simple calculation over 10,000 reports for two classifiers (e.g. w-SVM and NB for low-level patterns) with MERs equal to 0.10 and 0.04, respectively, would show an actual difference of 600 misclassified (either as potentially positive or as negative) reports between them. The actual cost in terms of extra workload would be those misclassified as potentially positive (based on our data that would be equal to 494 reports) but the actual cost in terms of safety surveillance would be those misclassified as negative (i.e. 106 reports). Based on our error analysis, less than 7% (7 out of 103) of the true positive cases would be falsely classified as negative for our best performing classifier, i.e. the rule-based classifier. We believe that this level of misclassification, in the context of the extensive known limitations of SRS, is probably acceptable, although we hope to engage in future efforts to refine our algorithm to reduce this even further. This further illustrates that one of the important properties of a classifier that is used to identify rare adverse events is high sensitivity because it returns a smaller number of falsely negative reports.

It could be argued that our approach lacks the automated feature extraction aspect, which has been previously reported as a strategy for TC (43). The issue of automatically extracting features that characterize the AE accurately requires care. The problem we are called to solve is the identification of rare or very rare events from the data at hand. Because features need to be related not only statistically but also causally to the outcome, informative feature selection better serves our purposes. The basis for our claim has been the availability of solid standards (i.e. Brighton case definitions) that are being used by physicians in their daily practice. Accordingly, the extraction of three feature representations supported the application of our multi-level approach. Thus, we treated the case reports not only as BOLs looking for lemmas (7) [Bag Of Words approach (stemmed or unstemmed) is rather limited (13)] but also as sources of patterns (low- and high-level); we extracted these patterns to examine their role in TC.

Informative feature selection mandated not only the use of Brighton criteria but also MOs' contributions since: i) certain criteria were not met in the case reports and should be excluded from the feature space, e.g. 'capillary refill time', ii) non-medical words were often used by patients to describe a symptom and should be included, e.g. the word 'funny' within variations of the phrase 'my throat felt funny' to describe 'itchy throat' or 'throat closure', and iii) other words raised a concern for further investigation even though they were not listed in Brighton definitions, e.g. 'epinephrine' or 'anaphylaxis'.

Regarding our TM methods, the construction of a controlled dictionary and lexicon is considered laborious, demanding, and costly because it relies on the recruitment of human experts (44). However, the informative development of a flexible and relatively small controlled dictionary/lexicon appeared to be very effective in our study. The same applied to the use of the dedicated semantic tagger. A part-of-speech tagger would assign non-informative tags to a span of text (i.e. symptom text in VAERS) that follows no common syntax; it would not support the grammar rules either. The grammar was also built in the same context: to better serve the extraction of the feature representations and facilitate both the rule-based classification and the training of ML classifiers.

Rule-based TC systems have been criticized for the lack of generalizability of their rules, a problem defined as 'knowledge acquisition bottleneck' (44). However, their value in handling specific conditions should not be ignored, such as in the Obesity NLP Challenge, where the top ten solutions were rule-based (27). ML methods are not as transparent as the rule-based systems but have been used extensively for TC (44). Our results showed that the rule-based classifier performed slightly better, probably due to the informative feature selection. Either rule-based or ML techniques could be applied to SRS databases and allow better use of human resources by reducing MOs' workload.

It could be argued that ensembles or a cascade of classifiers or even a modified feature space would handle the classification errors. Nevertheless, the principles of our study and the nature of VAERS would require the consideration of certain aspects prior to the application of such strategies. First, the construction of the feature space was based on the domain expert contribution; any alterations (use of new lemmas or introduction of new rules) should be approved accordingly to be valid. Second, a classification error will be always introduced by the Medical Officers who decide to acquire more information for a 'suspicious' report even if it does not meet all the criteria.

The methodology that was described in this paper and the discussion of the related aspects raises the interesting question of generalizability, i.e. the transfer of components to the identification of other AEFIs. The development of a broader medical lexicon and a set of basic rules could be suggested to support the extraction of all symptoms related to the main AEFIs, such as the Guillain-Barre Syndrome (GBS) and the Acute Disseminated Encephalomyelitis (ADEM). Based on these key components, other advanced rules representing the specific criteria per AEFI (as stated in Brighton definitions and described by MOs) could classify each report accordingly.

Our study lies partly in the field of text filtering since it investigated ways to automate the classification of streams of reports submitted in an asynchronous way (45). Generally, MOs' intention is two-fold: first, to identify the potentially positive and block the negative reports (step 1); second, to further classify those that proved to be positive into more specific categories (step 2), e.g., anaphylaxis case reports into levels of diagnostic certainty. This process is similar to the classification of incoming emails as 'spam' or 'non-spam' and the subsequent categorization of the 'non-spam' e-mails (46-48). Here, any further categorization would require the information gathering through the review of medical records that are provided in portable document format (pdf) only. The inherent difficulties related to the production of these files limit their usability and the possibility of utilizing this source remains to be investigated.

To conclude, our study demonstrated that it is possible to apply TM strategies on VAERS for TC purposes based on informative feature selection; rule-based and certain ML classifiers performed well in this context. It may be possible to extend the current work and to apply the same TM strategy regarding other AEs by incorporating experts' input in a semi-automated feature extraction framework.

FIG. 10 is an exemplary system suitable for performing exemplary embodiments of the invention. This system comprises a computer system 1000 comprising one or more processors 1010, one or more memories 1020 (comprising computer program code 1030), and one or more user input interfaces 1060 (e.g., network interfaces, touchscreen interfaces, mouse interfaces, keyboard interfaces, and the like). This example shows a display 1040 that also includes a user interface 1050. The user interface could show information such as the potentially positive reports or any other information described above that might be desired to be shown to a user. The computer readable code 1030, when executed by the one or more processors 1010, causes the computer system 1000 to perform the operations described herein.

Qualitative Error Analysis for Symptom Text

This section contains symptom text of the 15 reports and more details about their qualitative error analysis. The small number of FN reclassified reports does not allow the definition of firm misclassification patterns for any of the three classifiers. Interestingly, five reports (Reports 1-5, excluding BT for low-level patterns in the validation set; Supplementary Table 6) were misclassified by the three algorithms for all feature representations; these cases were picked as possible anaphylaxis based on the general context of the report and the MOs' concern for accessing more information in step 2. In five other cases (Reports 6-10; Supplementary Table 6) both w-SVM and BT classifiers failed to classify them as possible anaphylaxis using lemmas; the same was observed in three other cases (Reports 11-13; Supplementary Table 6) either for w-SVM or BT alone. On the other hand, the same reports were correctly classified by the three classifiers when using low- or high-level patterns. The remaining two reports were incorrectly misclassified by either the rule-based or all three classifiers using high-level (Report 14; Supplementary Table 6) and low- and high-level (Report 15; Supplementary Table 6) patterns, respectively; here, the existing elements could support the conceptual definition of high- and low-level patterns, however the text structure did not facilitate that for the rule-based classifier. The above observations showed that: (1) the low- and high-level patterns better supported the identification of a potentially positive anaphylaxis reports for w-SVM, BT and rule-based classifiers and (2) the falsely negatively classified reports after the reclassification could be explained by either the MOs concern for more information or the individual's reporting style that hid the existing anaphylaxis patterns.

SUPPLEMENTARY TABLE 6

Symptom text for the 15 reports of the testing and
validation set that were reclassified as truly positive:

| Report | Symptom Text |
|---|---|
| 1 | Pt. experienced "extreme pain" at the time of injection that radiated to her neck, back and chest. She became dizzy and nauseous 1 hour after injection, she developed hives all over her body - experienced "deep muscle pain" in her legs 5 hours after, she also c/o fatigue and an uncomfortable chest sensation. Leg pain is worsening and headache for 2 days. |
| 2 | Next day around 1pm experienced swelling in face and itchyness, hives in abdomen which was relieved by Benadryl. |
| 3 | Hands, arms itchy-raised hives hands, neck itchy, resp difficulty. 10:15 Mom notified of transport. Transported via rescue. |
| 4 | pt given H1N1 vaccine 20 min later she felt itchy, arm turning red, felt tongue enlarging. pt given 25 mg Benadryl 25 mg im, pt improved sent home on prn Benadryl and prednisone burst pack |
| 5 | After about 3-4 hours mother brought pt to voluntary ER. He developed generalized urticaria, he was complaining of difficulty breathing. Patient hx of allergic reaction (pluria rash) to PCN and AMOX. No above meds at the time. Rx BENADRYL, prednisone p.o. PEPCID too. |
| 6 | PT. c/o of pains to stomach and H/R - PT. did vomit approx. 1045. 1046 c/o hives, hives noted on bilateral forearms - 50 mg BENADRYL PO - vomited up. |
| 7 | Acute SOB and hives post vaccination. |
| 8 | Red skin, Itchy, Bright Red Blotches on neck, torso and groin, Trouble Breathing |
| 9 | Hives, puffy eyes, shortness of breath, hoarsey voice. |
| 10 | I started to have diffuclty breathing and started having Hives spread about my body |
| 11 | Throat became swollen and painful, vomited, stomach pains. The following information was obtained through follow-up and/or provided by the government. 12/16/2009 PCP records for 12/8 and 12/14/2009, patient with c/o's vomiting, mouth soreness, tongue swelling and urinary incontinence, tx'd with benadryl, was reported that child was ill prior to vaccine |
| 12 | hives, itching, red and hot face, a little difficulty breathing |
| 13 | Received H1N1 nasal~AM 12/29/2009. Taken to ER later that evening with hives and wheezing. No hx RAD no probs with seasonal flu mist & mom discussed this w/ me at her physical on 2/5/10. |
| 14 | About 10 mins after vaccines administered pt began to have trouble breathing, tongue swelling, wheezing. |
| 15 | Swelling of the face, throat, and eyes. Hives, rashes, and itching on day 2 |

Supplementary Table 7 includes the symptom text for the reports that were re-reviewed and classified as truly negative. The common characteristic of these reports is that the criteria for anaphylaxis were not fully met. Originally, MOs decided to classify them as positive for two main reasons: (1) they were extremely cautious to protect the safety of the public after receiving the signal from Canada and (2) based on that they wanted to acquire more information for any report that did not fulfill all the criteria but looked suspicious. However, in order to perform an accurate qualitative error analysis, MOs were asked to re-review the 36 falsely negatively classified reports following only the Brighton criteria for anaphylaxis. Consequently, our top classifiers appeared to have correctly classified these reports (Supplementary Table 7) as negative.

SUPPLEMENTARY TABLE 7

Symptom text for the 21 reports of the testing and
validation set that were reclassified as truly negative:

| Report | Symptom Text |
|---|---|
| 16 | Swollen tongue, difficulty breathing. The following information was obtained through follow-up and/or provided by the government. 1/29/10 Received medical information from patient: nausea. 1/28 and 1/29/2010 MR and DC summary for 1/18-1/20/2010 prior to vaccine administration and ED record for 1/26/2010 Dx Acute bronchitis patient with c/o's cold sx and productive cough |
| 17 | Received H1N1 on 1/26/10 @ 15:45. 1/27/10 about 1000 developed headache, fatigue congestion, sore throat. 1/28/10 afternoon, red puffy under eyes and hives front and back of trunk. Called HCP who advised BENADRYL. Hives resolved by 1/31/10. |
| 18 | 1. Dizziness. 2. Nausea Vomiting. 3. Hypertension. 4. Eye itchiness/redness/weakness. Treatment Drugs Used: 1-Diphenhydramine 2-Clonidine |
| 19 | Difficulty breathing after receiving seasonal flu mist and H1N1 shot. Required 3x hospital visits. Received 2x breathing treatments, prescribed rescue inhaler and steriods for broch. spasms 11/24 and 12/4/2009 ED records for 11/18/2009, Dx acute Bronchitis patient with c/o's SOB, chest pain. Tx: resp tx's with nebs |
| 20 | Increased heart beat and an odd cough - lasted about ½ hr but cough went into asthma and lasted about 1 week and have never had a reaction to any flu vaccine. |

SUPPLEMENTARY TABLE 7-continued

Symptom text for the 21 reports of the testing and
validation set that were reclassified as truly negative:

| Report | Symptom Text |
|---|---|
| 21 | 11/21/09 - Patient received H1N1 vaccination. While exiting facility, developed chest tightness, SOB, lightheaded, cyanotic lips and nail beds. BP 122/64-88-16. Patient remained seated until leaving facility via ambulance to local Emergency Dept. No resolution in symptoms. Work up in ED was negative. 12/7 & 12/8/09: ED Records recieved for dates of service 11/21/09. Dx: Probable vagal reaction, acute chest pain. Assessment: Presented after H1N1 vaccine with c/o chest tightness, tingling, anxiety, lightheadedness, SOB, cyanosis of nail beds and lips. SaO2 94%. Medicated with Ativan 0.5 mg. Pulse ox increased to 100% on room air. Felt well to go home. |
| 22 | Pt c/o hives, redness, and abdominal pain, 25 mg of PO Benadryl given. Update report information to include: Adverse evernt - Adominal pain right side. Shortness of breath. Sleepy. Mom did not take patient to pediatrician. |
| 23 | Emp. received H1N1 vaccine. States that approx 10 min later she began to feel hot and her palms became sweaty and she vomited x 2. |
| 24 | Headache, dry mouth, swollen eyes, rapid pulse, high blood pressure. The following information was obtained through follow-up and/or provided by the government. MR received 01/11/10 for DOS 12/16/09. Pt was not seen by PCP or ER/Hosp and headaches resolved after 2 days. |
| 25 | Headache - nausea all Hives 25 mg BENADRYL oral given w/good recovery |
| 26 | 1 c/o throat closing 2 transported by rescue to hospital The following information was obtained through follow-up and/or provided by the government. ED notes received 01/31/10 for DOS 11/02/09. DX: Allergic reaction. Pt presented with throat closing. Pt discharged home. |
| 27 | The following occurred two and half hours after receiving H1N1 shot 12/15/09. Difficulty breathing, rapid heart beat, the patient never experienced any heart problems prior to the vaccine. 12/31/09, 1/4/10, 1/6/10 Records received for ED, Hospital records and cardiology consult for dates of service 12/15/09 to 12/28/09. Dx: Atrial fibrillation with rapid ventricular rate. Two hours after H1N1 vaccine experienced chest tightness, SOB and palpitations. Took Benadryl and presented to ED in atrial fibrillation with ventricular rate of 147. Given Cardizem bolus and then drip. Experienced improvement of sx. of chest tightness, SOB, palpitations and control of heart rate. Successfully cardioverted and started on heparin. Discharged on coumadin and Lovenox. Followed up on 12/28/09 for persistent hypertension. Norvasc added to regimen. |
| 28 | Student c/o itching and warmth to L arm along with pain after H1N1 injection. Ice applied and mom notified. VS monitored. Cough began and student placed in supine position with feet elevated. BENADRYL given after itching and warmth noted. C/O dizziness - continued to monitor VS. C/O CP and nausea. The following information was obtained through follow-up and/or provided by the government. 1/7/2010 MD records for 12/15/2009 patient with c/o's lt arm itching and redness, dizziness, chest pain and nausea tx'd with Benadryl |
| 29 | Pt called office 1/12/10 AM to report that she had developed following symptoms last night @ 19:30: throat swelling, chest and back pain, blurry vision, irreg rapid heart rate, cough. She did not seek med. attention. Did not take antihistamines. All sx resolved without intervention. |
| 30 | Immediately became pale, dizzy, with tingling in throat, difficulty speaking, mind "fuzzy", difficulty hearing, nauseaus, difficulty breathing. Called doctor, took Benedryl, went with parents to ER where she received IV fluids, anti-nausea medications, steriods. Stayed in ER for 6 hours, continuing to be tired, nauseaus, dizzy 9 days later. The following information was obtained through follow-up and/or provided by the government. 1/25 and 1/29/2010 PCP notes, ED records for 1/9/2010, Dx adverse drug reaction, altered level of consciousness patient with c/o's dizziness, altered level of consciousness, difficulty speaking, pale and lethargic, tx IVF, IV Solu-Medrol |
| 31 | mild muscle pain on 15th, on 16th moderadte muscle pain, and on 17th and 18th sever muscle pain. Tylenol did not help. 3 200 mg ibuprofen helped about 50%. |
| 32 | Swelling of Throat approx. 5 hrs after vaccine admin. Fever day after vaccine admin. Hoarse, sore throat. Took diphenhydramine for swelling, ibuprofen for fever. |
| 33 | 1 - 10 min post injection - SOB/pale, bilateral wheeze. 2 - albuterol rescue inhaler x 2 - poor result 3 - 11:25 o2 via mask/albuterol neb x 1/911 to hosp 1/21/10 = TC "panic" attack re: parent. No problems residual pt. recovered |
| 34 | From the initial injection there was a problem. It didnt come out the needle at first and had to be tried again, pushing harder. It bunred immediately. Shortly after that, I began having stomach pains; heaviness in my arm where the injection site was; tingling in my fingers on that arm and a taste of metal in my mouth. I went to the walk in emergency room and the receptionist noted that my throat, neck and chest were red. When the doctor examined me, he also noted that I had a bad reaction to it because my arm was swollen and puffy. |
| 35 | Per pt had shortness of breath and itching. |
| 36 | high fever (104) Difficulty breathing fast heart beat Cold Hands Cold feet Paleness Blue lips Wheezing red eyes weakness runny nose dizziness |

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

REFERENCES (1) Sinha A, Hripcsak G, Markatou M. Large datasets in biomedicine: a discussion of salient analytic issues. Journal of the American Medical Informatics Association 2009; 16(6):759-67.
(2) Singleton J A, Lloyd J C, Mootrey G T, Salive M E, Chen R T. An overview of the Vaccine Adverse Event Reporting System (VAERS) as a surveillance system. Vaccine 1999; 17(22):2908-17.

(3) Ambert K H, Cohen A M. A System for Classifying Disease Comorbidity Status from Medical Discharge Summaries Using Automated Hotspot and Negated Concept Detection. Journal of the American Medical Informatics Association 2009; 16(4):590-5.

(4) Cohen A M. Five-way smoking status classification using text hot-spot identification and error-correcting output codes. Journal of the American Medical Informatics Association 2008; 15(1):32-5.

(5) Conway M, Doan S, Kawazoe A, Collier N. Classifying disease outbreak reports using n-grams and semantic features. International Journal of Medical Informatics 2009; 78(12):47-58.

(6) Farkas R, Szarvas G, Heged s I et al. Semi-automated construction of decision rules to predict morbidities from clinical texts. Journal of the American Medical Informatics Association 2009; 16(4):601-5.

(7) Mishra N K, Cummo D M, Arnzen J J, Bonander J. A Rule-based Approach for Identifying Obesity and Its Comorbidities in Medical Discharge Summaries. Journal of the American Medical Informatics Association 2009; 16(4):576-9.

(8) Ong M S, Magrabi F, Coiera E. Automated categorisation of clinical incident reports using statistical text classification. Quality and Safety in Health Care 2010 Aug. 19;doi: 10.1136/qshc.2009.036657.

(9) Savova G K, Ogren P V, Duffy P H, Buntrock J D, Chute C G. Mayo Clinic NLP system for patient smoking status identification. Journal of the American Medical Informatics Association 2008; 15(1):25-8.

(10) Solt I, Tikk D, Gal V, Kardkovacs Z T. Semantic classification of diseases in discharge summaries using a context-aware rule-based classifier. Journal of the American Medical Informatics Association 2009; 16(4):580-4.

(11) DeShazo J P, Turner A M. An interactive and user-centered computer system to predict physician's disease judgments in discharge summaries. Journal of Biomedical Informatics 2010; 43(2):218-23.

(12) Yang H, Spasic I, Keane J A, Nenadic G. A Text Mining Approach to the Prediction of Disease Status from Clinical Discharge Summaries. Journal of the American Medical Informatics Association 2009 July; 16(4):596-600.

(13) Cohen A M, Hersh W R. A survey of current work in biomedical text mining. Briefings in Bioinformatics 2005 March; 6(1):57-71.

(14) Hazlehurst B, Naleway A, Mullooly J. Detecting possible vaccine adverse events in clinical notes of the electronic medical record. Vaccine 2009; 27(14):2077-83.

(15) Melton G B, Hripcsak G. Automated detection of adverse events using natural language processing of discharge summaries. Journal of the American Medical Informatics Association 2005; 12(4):448-57.

(16) Murff H J, Forster A J, Peterson J F, Fiskio J M, Heiman H L, Bates D W. Electronically screening discharge summaries for adverse medical events. Journal of the American Medical Informatics Association 2003; 10(4):339-50.

(17) Wang X, Hripcsak G, Markatou M, Friedman C. Active computerized pharmacovigilance using natural language processing, statistics, and electronic health records: a feasibility study. Journal of the American Medical Informatics Association 2009; 16(3):328-37.

(18) Varricchio F, Iskander J, Destefano F et al. Understanding vaccine safety information from the vaccine adverse event reporting system. The Pediatric Infectious Disease Journal 2004; 23(4):287-94.

(19) Brown E G. Using MedDRA: implications for risk management. Drug Safety 2004; 27(8):591-602.

(20) Bousquet C, Lagier G, Lillo-Le Louet A, Le Beller C, Venot A, Jaulent M C. Appraisal of the MedDRA conceptual structure for describing and grouping adverse drug reactions. Drug Safety 2005; 28(1):19-34.

(21) Bonhoeffer J, Kohl K, Chen R et al. The Brighton Collaboration: addressing the need for standardized case definitions of adverse events following immunization (AEFI). Vaccine 2002; 21(3-4):298-302.

(22) Ruggeberg J U, Gold M S, Bayas J M et al. Anaphylaxis: Case definition and guidelines for data collection, analysis, and presentation of immunization safety data. Vaccine 2007 Aug. 1; 25(31):5675-84.

(23) Ewan P W. ABC of allergies: Anaphylaxis. British Medical Journal 1998; 316(7142):1442.

(24) Vellozzi C, Broder K R, Haber P et al. Adverse events following influenza A (H1N1) 2009 monovalent vaccines reported to the vaccine adverse events reporting system, United States, Oct. 1, 2009-Jan. 31, 2010. Vaccine 2010; 28(45):7248-55.

(25) Quality Investigation of Combo Lot Number A80CA007A of Arepanrix™ H1N1 (A503-Adjuvanted H1N1 Pandemic Influenza Vaccine) in Canada. Canadian Ministry of Health; 2010 Mar. 12.

(26) Reblin T. AREPANRIX™ H1N1 Vaccine Authorization for Sale and Post-Market Activities. Canadian Ministry of Health; 2009 Nov. 12.

(27) Uzuner O. Recognizing Obesity and Comorbidities in Sparse Data. Journal of the American Medical Informatics Association 2009; 16(4):561-70.

(28) Lewis D D, Ringuette M. A comparison of two learning algorithms for text categorization. Third Annual Symposium on Document Analysis and Information Retrieval 1994; 33:81-93.

(29) Carreras X, Marquez L. Boosting trees for anti-spam email filtering. 4th International Conference on Recent Advances in Natural Language Processing 2001.

(30) Platt J. Sequential minimal optimization: A fast algorithm for training support vector machines. Microsoft Research; 1998. Report No.: MST-TR-98-14.

(31) Hastie T, Tibshirani R, Friedman J. The elements of statistical learning. Second Edition ed. Springer; 2009.

(32) Stone C J, Hansen M H, Kooperberg C, Truong Y K. Polynomial splines and their tensor products in extended linear modeling. The Annals of Statistics 1997; 25(4):1371-425.

(33) Friedman J H. Regularized discriminant analysis. Journal of the American Statistical Association 1989; 84(405): 165-75.

(34) Rios G, Zha H. Exploring support vector machines and random forests for spam detection. Proceedings of the First Conference on Email and Anti-Spam (CEAS) 2004.

(35) Han E H, Karypis G, Kumar V. Text categorization using weight adjusted k-nearest neighbor classification. Advances in Knowledge Discovery and Data Mining 2001; 53-65.

(36) Chang C C, Lin C J. LIBSVM: a library for support vector machines. Department of Computer Science; National Taiwan University; 2001.

(37) Yang Y, Liu X. A re-examination of text categorization methods.: ACM; 1999 p. 42-9.

(38) Friedman M. The use of ranks to avoid the assumption of normality implicit in the analysis of variance. Journal of the American Statistical Association 1937; 32(200):675-701.

(39) Yang Y, Pedersen J O. A comparative study on feature selection in text categorization.: Citeseer; 1997 p. 412-20.

(40) Hinrichsen V L, Kruskal B, O'Brien M A, Lieu T A, Platt R. Using electronic medical records to enhance detection and reporting of vaccine adverse events. Journal of the American Medical Informatics Association 2007 November; 14(6):731-5.

(41) Jha A K, Laguette J, Seger A, Bates D W. Can surveillance systems identify and avert adverse drug events? A prospective evaluation of a commercial application. Journal of the American Medical Informatics Association 2008; 15(5):647-53.

(42) Linder J A, Haas J S, Iyer A et al. Secondary use of electronic health record data: spontaneous triggered adverse drug event reporting. Pharmacoepidemiology and Drug Safety 2010 Oct. 11; 19:1211-5.

(43) Forman G. An extensive empirical study of feature selection metrics for text classification. The Journal of Machine Learning Research 2003; 3:1289-305.

(44) Sebastiani F. Machine learning in automated text categorization. ACM Computing Surveys (CSUR) 2002; 34(1):1-47.

(45) Belkin N J, Croft W B. Information filtering and information retrieval: two sides of the same coin? Communications of the ACM 1992; 35(12):29-38.

(46) Androutsopoulos I, Koutsias J, Chandrinos K V, Spyropoulos C D. An experimental comparison of naive Bayesian and keyword-based anti-spam filtering with personal e-mail messages.: ACM; 2000 p. 160-7.

(47) Bekkerman R, McCallum A, Huang G. Automatic categorization of email into folders: Benchmark experiments on Enron and SRI corpora. Center for Intelligent Information Retrieval, Technical Report IR 2004; 418.

(48) Drucker H, Wu D, Vapnik V N. Support vector machines for spam categorization. IEEE Transactions on Neural networks 1999; 10(5):1048-54.

(49) Porter M F. An algorithm for suffix stripping. Program 1980; 14(3):130-7.

What is claimed is:

1. A method, comprising:
performing text mining on a set of case reports in text format to determine a set of grammar rules to be used to determine whether case reports meet a medical condition, the text mining comprising performing feature selection, used to determine the set of grammar rules, that combines standardized case definitions with experience of medical officers for the medical condition, wherein performing feature selection further comprises:
representing important keywords as features, the important keywords corresponding to the standardized case definitions for the medical condition and to information determined from the experience of medical officers for the medical condition;
determining low level patterns having major and minor criteria that included one or more of the keywords; and
creating high level patterns that comprise one or more of the major and minor criteria; and
outputting the set of grammar rules.

2. The method of claim 1, wherein the medical condition is anaphylaxis and the case reports are case reports corresponding to flu.

3. The method of claim 2, wherein the set of case reports is from a vaccine adverse event reporting system, and the anaphylaxis is caused by a flu vaccine.

4. The method of claim 1, wherein the standardized case definitions comprise Brighton Collaboration criteria.

5. The method of claim 1, wherein representing important keywords as features further comprises creating a list of lemmas to represent keywords of interest, and the method further comprises developing a lexicon for the medical condition and building a grammar based on the lexicon, wherein the building of the grammar forms the set of grammar rules.

6. The method of claim 5, further comprising using the set of grammar rules to support extraction of the major and minor criteria and the high level patterns from the case reports.

7. The method of claim 5, wherein the performing text mining is performed at a time prior to a current time and wherein the method further comprises at the current time applying the grammar rules to one or more new case reports to classify the one or more new case reports as either meeting the medical condition or not meeting the medical condition.

8. The method of claim 7, further comprising outputting one or more indications indicating whether the one or more new case reports are classified as meeting the medical condition or not meeting the medical condition.

9. The method of claim 7, wherein applying the grammar rules to one or more new case reports further comprises using a rule-based classifier to apply the grammar rules to the one or more new case reports to classify the one or more new case reports as either meeting the medical condition or not meeting the medical condition.

10. A computer program product comprising a non-transitory computer readable storage medium having computer readable program code embodied therewith, the computer readable program code configured to cause an apparatus to perform the following:
performing text mining on a set of case reports in text format to determine a set of grammar rules to be used to determine whether case reports meet a medical condition, the text mining comprising performing feature selection, used to determine the set of grammar rules, that combines standardized case definitions with experience of medical officers for the medical condition, wherein performing feature selection further comprises:
representing important keywords as features, the important keywords corresponding to the standardized case definitions for the medical condition and to information determined from the experience of medical officers for the medical condition;
determining low level patterns having major and minor criteria that included one or more of the keywords; and
creating high level patterns that comprise one or more of the major and minor criteria; and
outputting the set of grammar rules.

11. An apparatus, comprising:
one or more memories comprising computer readable code,
one or more processors, the one or more processors, responsive to execution of the computer readable code, to cause the apparatus to perform:
performing text mining on a set of case reports in text format to determine at least case reports indicated as meeting a medical condition, the text mining comprising applying a set of rules embodying features selected using both standardized case definitions for the medical condition and experience of medical officers for the medical condition, wherein performing feature selection further comprises:
representing important keywords as features, the important keywords corresponding to the standardized case definitions for the medical condition and to information determined from the experience of medical officers for the medical condition;

determining low level patterns having major and minor criteria that included one or more of the keywords; and creating high level patterns that comprise one or more of the major and minor criteria; and outputting at least the case reports being indicated as meeting the medical condition.

12. A method, comprising:

applying one or more grammar rules to one or more new case reports, the one or more grammar rules previously determined at least by performing text mining comprised of performing feature selection, used to determine the set of grammar rules, that combines standardized case definitions with experience of medical officers for the medical condition, wherein performing feature selection further comprised:

representing important keywords as features, the important keywords corresponding to the standardized case definitions for the medical condition and to information determined from the experience of medical officers for the medical condition;

determining low level patterns having major and minor criteria that included one or more of the keywords; and creating high level patterns that comprise one or more of the major and minor criteria; and outputting, based on the applying, one or more indications of whether the one or more new case reports meet or do not meet the medical condition.

13. The method of claim 12, wherein the medical condition is anaphylaxis and the case reports are case reports corresponding to flu.

14. The method of claim 13, wherein the set of case reports is from a vaccine adverse event reporting system, and the anaphylaxis is caused by a flu vaccine.

15. The method of claim 12, wherein the standardized case definitions comprise Brighton Collaboration criteria.

16. The method of claim 12, wherein representing important keywords as features further comprises creating a list of lemmas to represent keywords of interest, and the method further comprises developing a lexicon for the medical condition and building a grammar based on the lexicon, wherein the building of the grammar forms the set of grammar rules.

17. The method of claim 16, further comprising using the set of grammar rules to support extraction of the major and minor criteria and the high level patterns from the case reports.

18. The method of claim 12, wherein applying one or more grammar rules to one or more new case reports further comprises using a rule-based classifier to apply the grammar rules to the one or more new case reports to classify the one or more new case reports as either meeting the medical condition or not meeting the medical condition.

19. A computer program product comprising a non-transitory computer readable storage medium having computer readable program code embodied therewith, the computer readable program code configured to cause an apparatus to perform the following:

applying one or more grammar rules to one or more new case reports, the one or more grammar rules previously determined at least by performing text mining comprised of performing feature selection, used to determine the set of grammar rules, that combines standardized case definitions with experience of medical officers for the medical condition, wherein performing feature selection further comprised:

representing important keywords as features, the important keywords corresponding to the standardized case definitions for the medical condition and to information determined from the experience of medical officers for the medical condition;

determining low level patterns having major and minor criteria that included one or more of the keywords; and creating high level patterns that comprise one or more of the major and minor criteria; and outputting, based on the applying, one or more indications of whether the one or more new case reports meet or do not meet the medical condition.

20. An apparatus, comprising:

one or more memories comprising computer readable code, one or more processors, the one or more processors, responsive to execution of the computer readable code, to cause the apparatus to perform:

applying one or more grammar rules to one or more new case reports, the one or more grammar rules previously determined at least by performing text mining comprised of performing feature selection, used to determine the set of grammar rules, that combines standardized case definitions with experience of medical officers for the medical condition, wherein performing feature selection further comprised:

representing important keywords as features, the important keywords corresponding to the standardized case definitions for the medical condition and to information determined from the experience of medical officers for the medical condition;

determining low level patterns having major and minor criteria that included one or more of the keywords; and creating high level patterns that comprise one or more of the major and minor criteria; and outputting, based on the applying, one or more indications of whether the one or more new case reports meet or do not meet the medical condition.

* * * * *